United States Patent [19]

Castillo

[11] Patent Number: 4,940,044

[45] Date of Patent: Jul. 10, 1990

[54] KNEE BRACE INCORPORATING ADJUSTMENT MEANS TO ACCOMMODATE ANATOMICAL VARIATIONS OF THE KNEE JOINT AND LEG

[75] Inventor: James D. Castillo, Mission Viejo, Calif.

[73] Assignee: Innovation Sports, Inc., Irvine, Calif.

[21] Appl. No.: 308,117

[22] Filed: Feb. 8, 1989

[51] Int. Cl.$^5$ ............................................. A61F 3/00
[52] U.S. Cl. .................................. 128/80 C; 128/88; 623/39
[58] Field of Search ................. 128/80 B, 80 C, 80 F, 128/87 R, 88, 89 R; 623/39

[56] References Cited

U.S. PATENT DOCUMENTS 4,715,363 12/1987 Detty ............................... 128/80 C

FOREIGN PATENT DOCUMENTS 0297766 1/1989 European Pat. Off. .......... 128/80 C

*Primary Examiner*—Robert A. Hafer
*Assistant Examiner*—Lynda M. Cofsky
*Attorney, Agent, or Firm*—Stetina and Brunda

[57] ABSTRACT

A brace for supporting a knee joint is disclosed specifically adapted for use in athletic, i.e. sports, applications. The brace is formed by a pair of frame members disposed on opposite sides of the knee joint which are pivotally connected adjacent one end by way of ratio-swing hinge members. Each of the frame members are pivotally connected via a flapper hinge adjacent their opposite end to a support cuff/pad adapted to be affixed to the user's leg adjacent the tibia and femur, respectively. The lateral position of the flapper hinges may be adjusted to accommodate for bowlegged or knock-kneed conditions of the user. Means are additionally provided between the tibia cuff and its respective frame member to allow plane adjustment between the tibia and femur of the user. The femur frame member is formed to include a convex-shaped portion specifically sized to extend over the attachment point of the vastas medialas muscle and thereby readily accommodate differing users.

14 Claims, 3 Drawing Sheets

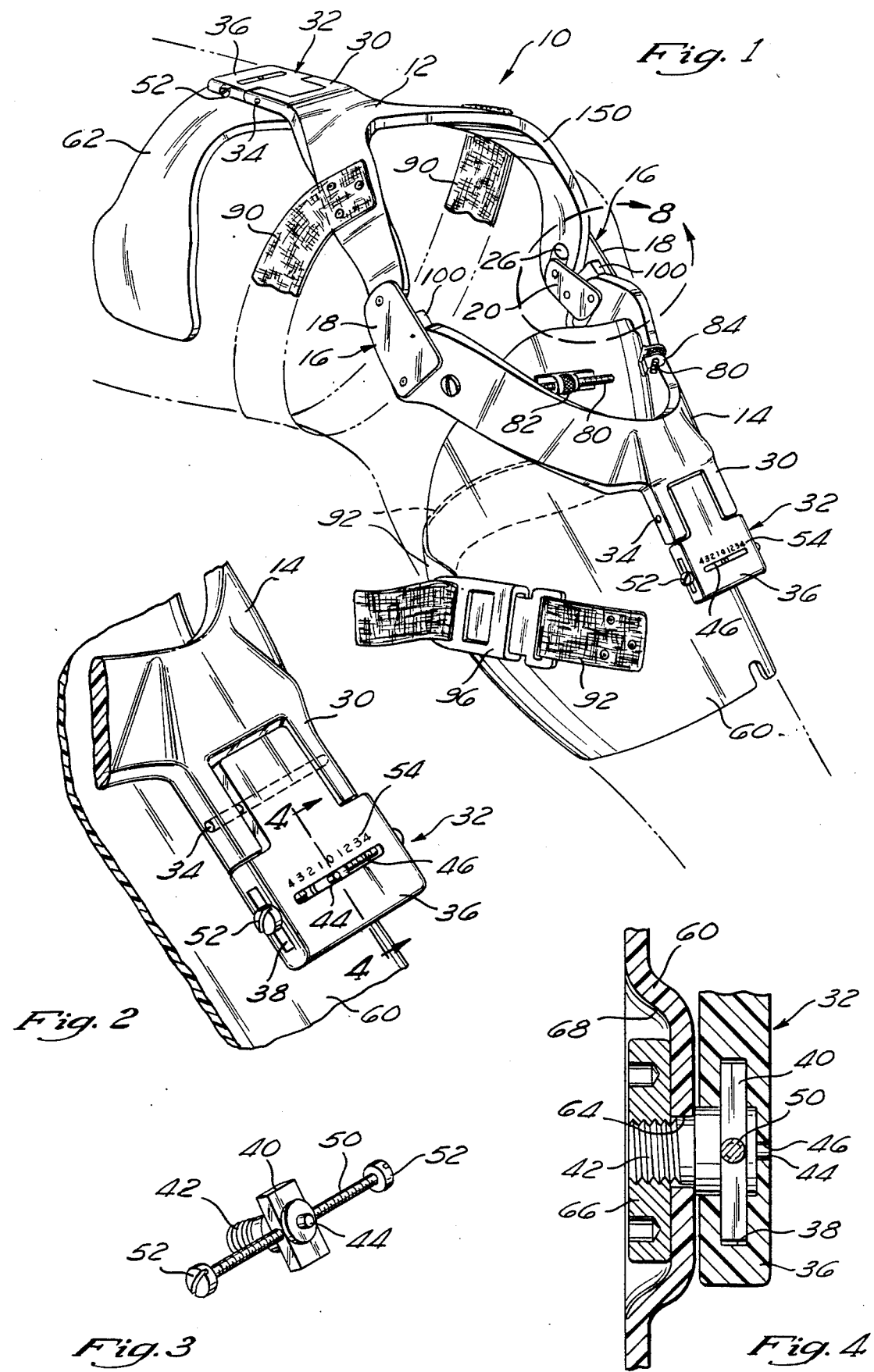

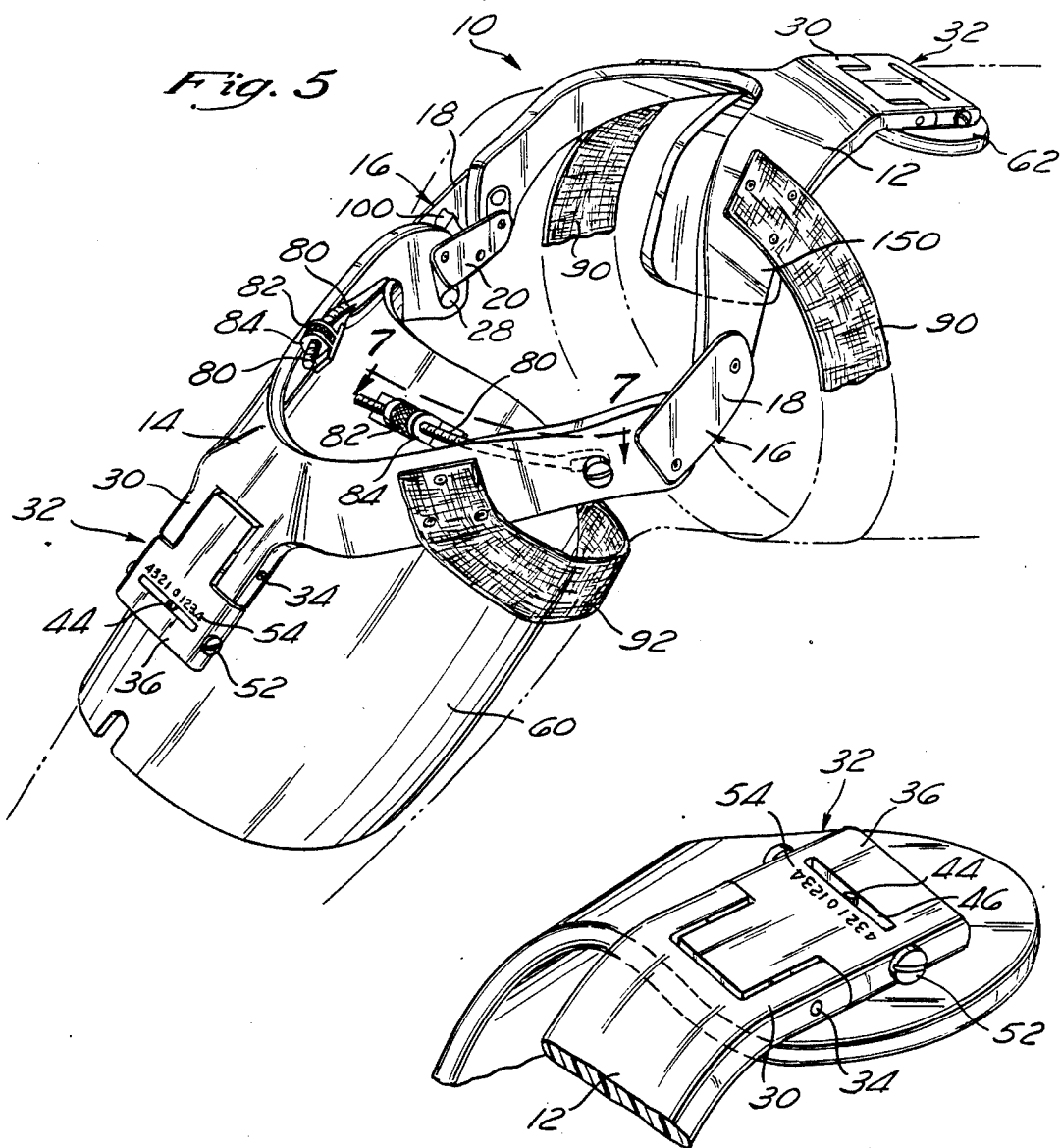

KNEE BRACE INCORPORATING ADJUSTMENT MEANS TO ACCOMMODATE ANATOMICAL VARIATIONS OF THE KNEE JOINT AND LEG

FIELD OF THE INVENTION

The present invention relates to braces for supporting joints, and more particularly, to a knee brace specifically adapted for use in athletic, i.e. sports, applications.

BACKGROUND OF THE INVENTION

As is well known, the knee joint, although frequently considered a hinge joint, actually comprises two joints, lateral and medial, between the femur and tibia, and one arthrodial joint between the patella and femur. The primary movements of the knee comprise flexion, i.e. rearward rotational movement of the tibia relative the femur, and extension, i.e. forward rotational movement of the tibia relative the femur.

The flexion and extension movements of the knee joint are not simply pivotal movements about a fixed axis. During flexion, the axis around which movement takes place shifts backward, and during extension it shifts forward. This is different from a more typical hinge joint, such as an elbow, where the axis of rotation does not shift. As full extension is reached, the tibia is rotated inward or rearward and the joint in effect is disposed in a "locked" position with the ligaments taut. This gives the joint greater stability in the extended position. As flexion is initiated, the tibia initially lowers or moves downwardly with a small external rotation of the tibia which "unlocks" the joint and subsequently the tibia rotates or rolls about the joint to full flexion. Accordingly, the initial unlocking of the knee joint during flexion proceeds actual full rotation of the knee.

Due to the above complexity of knee movement, for a brace to more fully support the knee joint of the user and facilitate rehabilitation and/or prevent re-injury of an injured knee joint, the brace must more closely analogize the movement of the knee than a simple hinge mechanism. Additionally, with specific relation to athletic or sports applications, the requirement for such analogized movement becomes acute. Further, for such sports applications, a knee brace must be relatively lightweight to avoid over constriction which reduces success in the athletic endeavor yet possess sufficient structural strength to adequately support the knee joint during impact thereupon.

In recognizing the need for an effective sports knee brace, various knee braces have been introduced into the marketplace. Such contemporary knee braces, however, have generally failed to provide the precise simulation of knee joint movement, as described above or have comprised relatively heavy, bulky apparatus thereby detracting from the user's athletic endeavor. Further, such contemporary designs have typically failed to possess sufficient structural integrity to prevent re-injury of the knee joint as may be occasioned by impact to the knee joint during physical sport endeavors.

Additionally, most contemporary sports braces have further been deficient in that the vertical plane of the brace and other physical parameters of the brace have been at the time of manufacture and hence have proven unsuitable for individual users having different curvatures or conditions of the leg at the level of the knee. Such conditions are commonly attributable to an imbalance between the medial and lateral support of the knee. Lack of adequate lateral support of the knee may produce a bowlegged condition, i.e. outward curvature of the leg adjacent the level of the knee. A lack of medial support of the knee may produce a knock-kneed condition, characterized by an inward curvature of the leg at the level of the knee. As such, a brace designed for individuals having normal curvature of the leg at the level of the knee may therefore be uncomfortable or entirely unsuitable for bowlegged or knock-kneed individual users.

In recognizing these inherent deficiencies, the vast majority of contemporary knee braces have been manufactured on a prescription, i.e. one of a kind basis, to properly accommodate the differing physical parameters of the user. Such unique one of a kind fabrication significantly increases overall costs of the knee brace as well as increases delivery time of braces to the individual user. Consequently there exists a substantial need for a knee brace that may be manufactured to accommodate differing users and be subsequently adjusted at the time of placement or installation upon the user to properly support the knee of the user having various degrees of leg curvature and leg conditions at the level of the knee.

SUMMARY OF THE PRESENT INVENTION

The present invention specifically addresses and alleviates the above-referenced deficiencies associated in the prior art. More particularly, the present invention comprises a brace for supporting a knee joint which, although not limited thereto, is specifically adapted for use in athletic, i.e. sports, applications.

The brace is formed by a pair of frame members disposed on opposite sides of the knee joint which are pivotally connected adjacent one end thereof by way of ratio swing hinge members The ratio swing hinge members are specifically designed to closely simulate rotational movement of the tibia relative the femur whereby the pivot point of the hinge varies or changes during rotational movement of the tibia relative the femur. As such, the knee brace of the present invention closely simulates normal knee movement, thereby enhancing rehabilitation and preventing injury to the knee during use. In the preferred embodiment, each of the frame members is formed of a high strength, lightweight composite material possessing sufficient strength to adequately support the knee joint even during physical impact associated with sports endeavors, yet be sufficiently lightweight so as not to deter from the performance of the physical endeavor.

Each of the frame members are provided with a flapper hinge adjacent their distal ends which pivotally connect the frame members to a support cuff or pad adapted to be affixed to the user's leg adjacent the tibia and femur, respectively, by use of one or more straps. The flapper hinges include adjustment means associated thereon which allow the lateral position of the flapper hinges to be adjusted relative the cuff and pad. As such, the knee brace of the present invention specifically accommodates bowlegged or knock-kneed conditions of the user.

The present invention additionally incorporates a manual adjustment means between the tibia cuff and its respective frame member which permits plane adjustment between the tibia and the femur of the user. Such plane adjustment insures that the support cuff is maintained parallel to the soft tissue adjacent the tibia during use and the lateral pad is maintained parallel to the soft tissue adjacent the femur of the user, thereby properly supporting the user's knee joint during use.

So as not to hamper the physical endeavor yet prevent any hyper-extension of the knee joint during use, the brace of the present invention incorporates a unique stop mechanism into the ratio swing hinges of the frame members. In the preferred embodiment, the stop mechanism comprises differing sized stop inserts which may be rapidly inserted into the hinges to restrict extension without restricting flexion of the knee joint. Preferably the stop inserts are formed as progressively sized elements which serve to limit extension in varying degree segments, such as 5 degrees, 10 degrees, 15 degrees, and 20 degrees. As such, during rehabilitation of the knee, differing stop inserts may be progressively utilized to allow greater extension as desired.

In the preferred embodiment, the upper frame member is formed to include a convex-shaped portion which extends upwardly and outwardly adjacent the inside region of the knee joint. This particular convex configuration is utilized such that the frame member extends over the attachment point of the vastus medialis muscle as opposed to extending over the central or belly portion of the muscle. Since the vastus medialis muscle varies substantially between athletic users, the incorporation of the convex portion of the frame member allows the knee brace to accommodate and be readily utilized upon differing users. In this regard, due to the specific design and adjustment features incorporated into the present invention, the present invention may be formed in three fixed medial sizes, i.e. fixed in relation to the distance between the ratio swing hinges of the present invention (i.e. to accommodate knee width size), which three fixed sizes may subsequently be adjusted at the time of positioning upon the user to accommodate nearly all users.

Additionally, the present invention incorporates a novel strap arrangement which attaches the lower cuff to the lower frame member in an angular orientation which serves to support the knee even during side load impact conditions.

DESCRIPTION OF THE DRAWINGS

These as well as other features of the present invention will become more apparent upon reference to the drawings wherein:

FIG. 1 is a perspective view of the knee brace of the present invention installed upon the right leg of a user;

FIG. 2 is an enlarged partial perspective view of the flapper hinge connection of the frame members to the support cuff/pad;

FIG. 3 is a perspective view of the lateral adjustment mechanism incorporated into the flapper hinge of FIG. 2;

FIG. 4 is a cross-sectional view taken about line 4—4 of FIG. 2;

FIG. 5 is a perspective view of the knee brace of the present invention disposed upon the leg of a user from a side opposite to that shown in FIG. 1;

FIG. 6 is an enlarged partial perspective view of the flapper hinge disposed upon the lateral pad of the present invention;

FIG. 7 is a cross-sectional view taken about line 7—7 of FIG. 5 illustrating the tibia cuff/frame member adjustment means;

DETAILED DESCRIPTION OF THE PREFERRED EMBODIMENT

Figure 8:
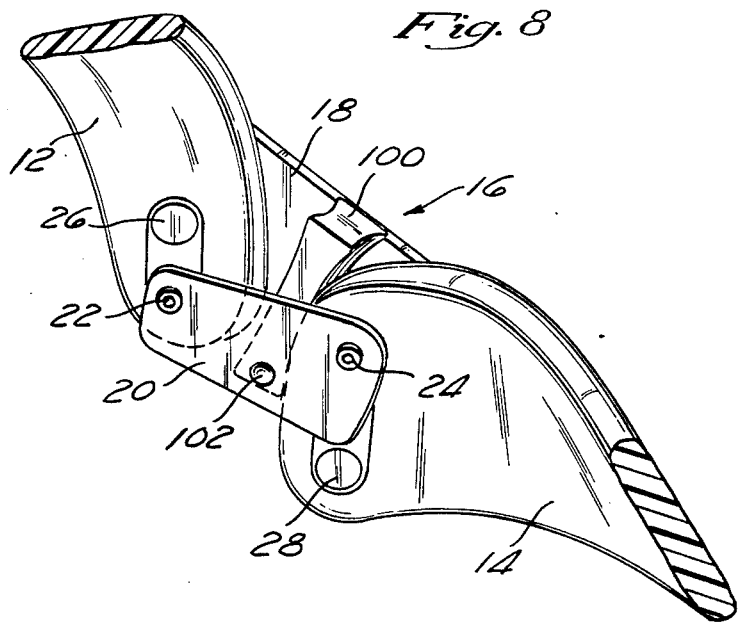
FIG. 8 is an enlarged partial perspective view illustrating the ratio swing hinge mechanism attached to the frame members and depicting the insertible flexion stop member disposed therein.

The description set forth below in connection with the appended drawings is intended merely as a description of the presently preferred embodiment of the invention, and is not intended to represent the only form in which the present invention may be utilized. The description sets forth the functions and structural elements of the invention in connection with the illustrated preferred embodiment. It will be understood, however, that the same or equivalent functions and advantages of the present invention may be accomplished by different embodiments which are encompassed within the spirit and scope of the present invention.

Referring to the drawings, the knee brace 10 of the present invention, specifically adapted for athletic, i.e. sports, applications, is depicted. For purposes of illustration the knee brace 10 is illustrated in a right-leg embodiment worn upon the right leg of a user. However, it will be recognized that the invention additionally is applicable to left-leg embodiments with the structure of the brace 10 being the same but reversed in orientation. As best shown in FIGS. 1 and 5, the knee brace 10 is composed of a pair of generally Y-shaped frame members 12 and 14 which are disposed in an inverted relative orientation and positionable on opposite sides of the knee joint of a user. In the preferred embodiment, both of the pair of members 12 and 14 are formed from a fiber reinforced composite material having sufficient rigidity to withstand impact forces encountered during physical sport endeavors yet be sufficiently light in weight so as not to impair the physical sport activity. However, other materials such as metal or plastic are contemplated herein.

Figure 9A:
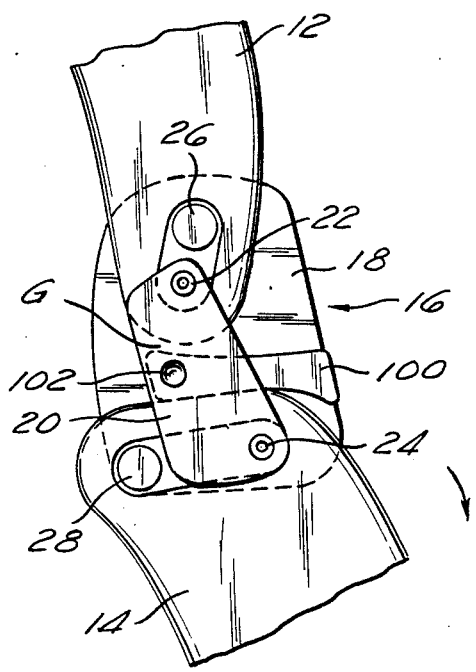
FIG. 9A is a partial perspective view of the pair of frame members and ratio swing hinge depicting the relative position of the frame members, hinge, and stop insert member during flexion of the knee joint.
Figure 9B:
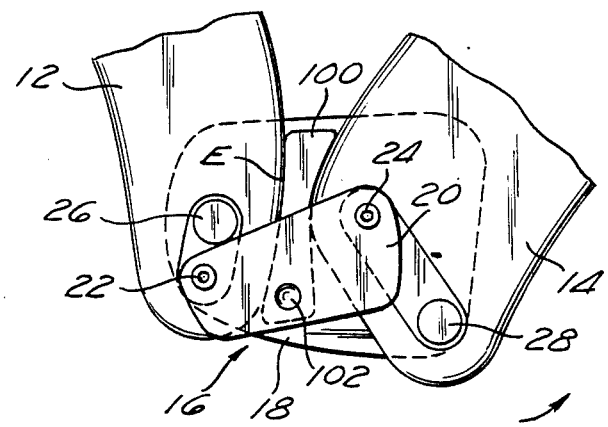
FIG. 9B is a perspective view of the frame members' ratio swing hinge and stop insert member depicting the relative position of the same during extension of the knee joint.

The frame members 12 and 14 are pivotally connected to one another by a pair of ratio swing hinges 16, each composed generally of an exterior plate member 18 and interior linking member or linking plate 20. As best shown in FIGS. 8, 9A, and 9B, the linking plate 20 is pivotally mounted to the frame members 12 and 14 via pins 22 and 24, respectively, while the exterior plate member 18 is pivotally mounted to the frame members 12 and 14 by pivot pins 26 and 28, respectively. Due to the positioning of the pivot pins upon the base plate 18, linking plate 20, and frame members 12 and 14, the hinges 16 provide a ratio swing movement between the frame members 12 and 14 as the frame members 12 and 14 are articulated relative one another. A more thorough description of the operation of the ratio swing hinges 16 is disclosed in pending U.S. patent application Ser. No. 07/068,030, filed June 29, 1987, entitled Knee Brace and assigned to the assignee of the subject application, the disclosure of which is expressly incorporated herein by reference The use of the ratio swing hinges 16 allows relative movement of the frame members 12 and 14 in a regulated manner varying pivot axis which simulates normal knee movement wherein during initial movement of the tibia relative the femur in flexion, the tibia slightly lowers to "unlock" the knee joint and once "unlocked" subsequently pivots rapidly backward in flexion. Although in the preferred embodiment, the present invention utilizes the ratio swing hinges 16, those skilled in the art will recognize that other hinge designs may be substituted therefor and are contemplated herein.

The upper-most and lower-most end of the upper and lower frame members 12 and 14, respectively, terminate in a U-shaped yoke 30 which forms a first portion of a flapper hinge member assembly, designated generally by the numeral 32. As shown, the yoke 30 is pivotally mounted via a pivot pin 34 to a base portion 36 of the flapper hinge 32. The base portion 36 is provided with a rectangular-shaped elongate central cavity 38 (best shown in FIGS. 2 and 4), which slidably receives therein a complementary-shaped carriage 40 (shown in FIG. 3). The carriage 40 is provided with a threaded shank 42 extending downwardly therefrom and an indicator post 44 extending upwardly therefrom. The post 44 is sized to be received within an elongate slot 46 formed within the upper surface of the base portion 36. A lead screw 50 is threadingly engaged through the carriage 40 and extends throughout the length of the cavity 38 terminating in a pair of screwdriver heads 52 positioned on opposite sides of the base portion 36. The base portion 36 is additionally provided with indicia 54 printed on its top surface thereof which, in the preferred embodiment, comprises scaled units corresponding to the position of the indicator post 44 within the elongate slot 46. As will be recognized, by such a structure, the flapper hinge member assembly 32 allows pivotal movement of the frame members 12 and 14 relative their respective base member 36 about the axis of the pivot pin 34. Additionally, by manual turning of the lead screw 50 by way of a screwdriver (not shown) engaging the screwdriver heads 52, the lateral position of the carriage 40 relative the base member 36 of the flapper hinge 32 may be varied as desired.

The flapper hinge 32 of the lower frame member 14 is mounted to a semi-flexible plastic cuff 60 which is preformed to be positionable about the soft tissue of a user's leg adjacent the tibia Similarly, the flapper hinge 32 of the upper frame member 12 is mounted to a lateral pad 62, preferably formed having a rigid construction and sized to extend inwardly upon the soft tissue of the user adjacent the femur. In the preferred embodiment, the flapper hinges 32 are mounted to the cuff 60 and lateral pad 62 in a similar fashion, as depicted in FIG. 4. As shown, threaded shank 42 of the carriage 40 extends through a complimentary-sized aperture 64 formed through the cuff 60 and pad 62 and is threaded into a spanner fastener 66 positioned on the under-surface of the cuff 60 and pad 62. So as to avoid any discomfort to the user, the pad 62 and cuff 60 is provided with a concave recess 68 formed on their lower surface, the depth of which is equal or slightly greater than the height of the spanner fastener 66.

The upper portion of the cuff 60 is additionally secured to the lower frame member 14 by a pair of elongate threaded members 80. As best shown in FIGS. 1, 5, and 7, the elongate threaded member 80 comprises a flexible threaded shaft, one end of which is affixed to the lower frame member 14 via a threaded fastener 16 extending therethrough and the opposite end of which threadingly engages a knurled thumb wheel 82 mounted to the exterior surface of the cuff 60 via a mounting block 84. As shown, the mounting block 84 is affixed to the exterior surface of the cuff 60 via plural threaded fasteners 86.

By such an arrangement, it will be recognized that the relative pivotal position of the upper portion of the cuff 60 relative the frame member 14 may be varied by manual turning of the thumb wheels 82 on both of the lead screws 80. In this regard, during tightening of the thumb wheels 82 upon the lead screw 80, the cuff 60 via its interconnection with the carriage 40, is free to pivot about the pivot pin 34 of the flapper hinge 32 and approach or be in close proximity to the frame member 14. Alternatively, by loosening of the thumb wheels 82 upon the lead screws 80, the cuff 60 may pivot about the pivot pin 34 to extend further away from the frame member 14 adjacent its upper-most end As will be discussed in more detail infra, such adjustment allows the brace 10 to accommodate differences in the vertical plane between the femur and tibia of the user.

As shown, the brace 10 of the present invention is preferably attached to the user's leg via a pair of straps 90 and 92. Preferably, the strap 90 is attached directly to the upper frame member 12 and is adapted to extend about the soft tissue of the user adjacent the femur. The strap 92 is preferably affixed to the lower portion of the cuff 60 and is adapted to extend behind the soft tissue of the user adjacent the tibia and additionally is securely attached to the lower frame member 14 on the upper portion of the same. As such, the lower strap member 92 extends angularly from the inner portion of the calf to the lower portion of the calf in a manner depicted. To allow adjustment of the strap 92, an adjustment member and clasp 96 may be provided on both strap members 90 and 92, although only depicted in relation to strap member 92. Additionally, although not shown, one or more additional strap members or elastic bands may be provided to secure the cuff 60 and lateral pad 62 to the soft tissue of the user.

Referring more particularly to FIGS. 8, 9A, and 9B, it may be seen that the ratio swing hinges 16 are specifically designed to mount a stop member insert 100 between the distal ends of the frame members 12 and 14. In the preferred embodiment, the stop member insert 100 comprises an elongate plastic member which is retained between the linking member 20 and plate member 18 of the hinge 16 by way of a dimple protuberance 102 formed upon the linking member 20 which engages a complimentary-shaped concave recess formed on the stop member insert 100. The effective width of the stop member 100 is sized as desired to form a physical stop or barrier which prohibits relative movement between the frame members 12 and 14 in extension movement of the knee yet insures free movement between the frame members 12 and 14 in flexion.

The interaction of the stop member insert 100 relative the frame members 12 and 14 is depicted in FIGS. 9A and 9B. In FIG. 9A, the relative position of the distal ends of the frame members 12 and 14 and stop member 100 is depicted when the knee brace is in full flexion. As shown, a gap G exists between the upper surface of the stop member 100 and the lower distal end of the upper frame member 12 whereby the frame member 14 may be articulated in a direction indicated by the arrow in FIG. 14 without any prohibition. Alternatively, during extension of the knee, the lower frame member 14 travels in the direction indicated by the arrow in FIG. 9B whereby the upper surface of the stop member insert 100 contacts, i.e. abuts, the upper frame member 12 along its edge E, whereby the stop member insert 100 prohibits any further extension of the knee, i.e. prohibits further movement of the lower frame member 14 in the direction indicated by the arrow in FIG. 9B. In the preferred embodiment, the effective width of the stop member insert 100 may be varied by supplying differing-sized stop member insert 100 with the brace 10, which differing-sized stop member inserts 100 being sized to progressively limit the degree of extension of the knee, i.e. 5 degrees extension, 10 degrees extension, 15 degrees extension, etc. As such, the present invention accommodates rehabilitation and prevents hyperextension of the knee by allowing a user to progressively increase the extension allowed by the knee brace merely by inserting differing-sized stop member inserts 100 within the ratio swing hinges 16.

With the structure defined, the operation of the knee brace 10 of the present invention may be described. Initially, the knee brace 10 is positioned about the user's leg in a manner depicted in FIG. 1 and 5. Initial sizing of the brace 10 for the user is facilitated merely by insuring that the distance between the ratio swing hinge members 16 is slightly greater than the medial lateral width of the knee joint such that the hinges 16 are disposed on opposite sides of the knee joint in close proximity thereto. In this regard, the applicant has found that three sizes of the knee brace 10, i.e. small, medium, and large, gaged by the medial lateral width of the brace, is sufficient to allow the brace 10 to accommodate nearly all users. Such sizing of the brace 10 is additionally facilitated by the specification formation of the upper frame member 12 to include a convex portion 150, depicted in FIGS. 1 and 5, which is formed to have convex configuration such that the frame portion 150 extends upwardly over the attachment point of the vastus medialis muscle of the user as opposed to the main portion or belly portion of the muscle. In this regard, the vastus medialis muscle varies substantially between users and in particular athletes which heretofor has prevented standardized sized braces to accommodate differing muscle tones in the user.

With the proper sized brace 10 chosen and positioned upon the user's leg, the upper strap member 90 may be tightened to cause the lateral pad 62 to be firmly affixed about the soft tissue of the user adjacent the femur. Subsequently, the lower strap member 92 may be tightened in an analogous manner whereby the lower cuff 60 is securely fastened to the soft tissue of the user's leg adjacent the tibia. Since the vertical plane, i.e. the vertical relationship between a user's femur and tibia varies substantially between users, the thumb wheels 80 may be manually turned to either tighten or loosen the lead screws 80 thereby insuring that the pad 60 contacts the user's soft tissue about the tibia throughout the length of the cuff 60. As will be recognized, during such adjustment of the thumb wheels 82 upon the lead screws 80, the cuff 60 is permitted to pivot about the pivot pin 34 of the lower flapper hinge 32. As such, the brace 10 insures that the lateral pad 62 is maintained parallel to the femur and the cuff 60 is maintained parallel to the tibia when positioned upon the user.

Subsequently, the position of the cuff 60 and lateral pad 62 relative the frame members 12 and 14 may be adjusted by manually turning the screwdriver head 52 of the lead screw 50 of the flapper hinges 32 so as to accommodate bow-legged and/or knock-kneed conditions of the user. As will be recognized, during such adjustment, the pad 62 and cuff 60 are reciprocated laterally relative the hinges 32 Depending upon the desired permitted extension of the knee, a properly sized stop member insert 100 may then be inserted into each of the ratio swing hinges 16 in a manner previously described, thereby insuring that hyperextension of the knee is prohibited.

As will be recognized, by installing the brace 10 upon the user, the brace 10 accommodates differences in the vertical plane between the femur and tibia of the user, accommodates bow-legged and knock-kneed conditions of the user, facilitates proper regulated movement of the knee due to the ratio swing hinges 16, and prohibits hyperextension of the knee by way of the stop member inserts 100. Further, in view of the diagonal positioning of the lower strap member 92 upon the cuff 60 and lower frame member 14, the tibia of the user's leg is securely supported by the lower frame member 14 from lateral impact typically occasioned in physical sports, such as football, basketball, and soccer. As such, the brace 10 of the present invention significantly reduces reinjuring of the knee joint by impact caused in such physical activities.

Although for purposes of illustration, certain materials, components, and structural embodiments have been depicted, those skilled in the art will recognize that various modifications to the same can be made without departing from the spirit of the present invention, and such modifications are clearly contemplated herein.

What is claimed is:

1. A knee brace comprising:
   a pair of frame members sized to be positionable in an inverted relative orientation above and below the knee joint of a user with the end portions of said frame members disposed laterally on opposite sides of the knee joint and the central portion of said frame members disposed adjacent the front of the user's leg;
   a pair of hinge members disposed substantially adjacent the knee joint and connected to the end portions of said frame members to pivot said frame members about the knee joint;
   a first and second support member removably attachable to the front of the user's leg above and below the knee joint;
   a flapper hinge member mounted to each of said first and second support members engageable with a respective one of said pair of frame members to affix and permit rotational movement of each of said frame members about an axis generally parallel to the pivot axis of said pair of hinge members, said rotational movement allowing said knee brace to accommodate plane variance conditions of the user's leg; and
   means formed on said flapper hinge member for varying the lateral position of said first and second support member relative said pair of frame members, said means comprising a carriage slidably positioned on said flapper hinge member and mounted to each of said first and second support members.

2. The knee brace of claim 1 further comprising a lead screw carried by said flapper hinge member and threadingly engaged with said carriage to slidably reciprocate said carriage laterally along the length of said flapper hinge member.

3. A knee brace comprising:
   a pair of frame members sized to be positionable in an inverted relative orientation above and below the knee joint of a user with the end portions of said frame members disposed laterally on opposite sides of the knee joint and the central portion of said frame members disposed adjacent the front of the user's leg;

a pair of hinge members disposed substantially adjacent the knee joint and connected to the end portions of said frame members to pivot said frame members about the knee joint;

a first and second support member removably attachable to the front of the user's leg above and below the knee joint;

a flapper hinge member mounted to each of said first and second support members engageable with a respective one of said pair of frame members to affix and permit rotational movement of each of said frame members about an axis generally parallel to the pivot axis of said pair of hinge members, said rotational movement allowing said knee brace to accommodate plane variance conditions of the user's leg; and a pair of flexible threaded members affixed at one end to said frame member positioned below the knee joint and engageable at the opposite end to a threaded connector mounted to said second support member.

4. The knee brace of claim 3 wherein said threaded connector comprises a thumb wheel carried on a mounting block affixed to said second support member.

5. The knee brace of claim 4 wherein said second support member comprises a semi-rigid member contoured to conform to the front of a user's leg.

6. The knee brace of claim 5 wherein said first support member comprises a rigid lateral pad formed to conform to the front of the user's leg.

7. The knee brace of claim 6 wherein each of said pair of frame members is formed having a generally Y-shaped configuration.

8. The knee brace of claim 7 wherein the frame member positioned above the knee joint of the user includes a convex portion sized to extend over the knee attachment location of the vastus medialis muscle of the user.

9. The knee brace of claim 8 further comprising a strap member mounted to said frame member positioned below the knee joint of the user and extensible angularly downward about the back of the user's leg and connected to said semi-rigid member.

10. A knee brace comprising:

a first pair of generally Y-shaped frame members, each comprising a singular central portion which bifurcates to two end portions, said Y-shaped members being sized to be positionable in an inverted relative orientation above and below the knee joint of the user with the end portions of said frame members disposed laterally on opposite sides of the knee joint and the central portion of each said frame member disposed adjacent the front of the user's leg;

a pair of hinge members disposed substantially adjacent the knee joint and connected to the end portions of said frame members such that said frame members may pivot about a primary pivot axis to allow bending of the knee joint;

a lateral pad removably attachable to the front of the user's leg above the knee joint;

a cuff removably attachable to the front of the user's leg below the knee joint; and first and second flapper hinge members mounted to said lateral pad and said cuff respectively, each said flapper hinge member being engageable with the central portion of a respective one of said pair of frame members in such manner as to permit pivotal movement of said frame members about upper and lower secondary pivot axes generally parallel to said primary pivot axis;

said pivotal movement about said secondary pivot axes being operative to permit said knee brace to accommodate plane variance conditions of the user's leg.

11. The knee brace of claim 10 further comprising means formed on said flapper hinge member for varying the lateral position of said hinge member relative said lateral pad and said cuff to permit the knee brace to accommodate knock-kneed and bow-legged conditions of the user's leg.

12. The knee brace of claim 11 further comprising means extending between said frame member positioned below the knee joint of the user in said cuff for varying the rotational position of said cuff relative said frame member.

13. The knee brace of claim 12 further comprising means formed on said pair of hinge members for regulating the relative pivotal movement of said pair of frame members.

14. The knee brace of claim 13 further comprising means formed on said pair of hinge members for limiting the extension of said pair of frame members.

* * * * *